(12) United States Patent
Todoroki et al.

(10) Patent No.: US 11,864,885 B2
(45) Date of Patent: Jan. 9, 2024

(54) BIOLOGICAL STATE MONITORING SYSTEM

(71) Applicants: MINEBEA MITSUMI INC., Nagano (JP); NATIONAL UNIVERSITY CORPORATION CHIBA UNIVERSITY, Chiba (JP)

(72) Inventors: Shinsuke Todoroki, Fukuroi (JP); Shiroh Isono, Chiba (JP)

(73) Assignees: MINEBE MITSUMI INC., Nagano (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 0 days.

(21) Appl. No.: 17/050,292

(22) PCT Filed: Apr. 15, 2019

(86) PCT No.: PCT/JP2019/016128
§ 371 (c)(1),
(2) Date: Oct. 23, 2020

(87) PCT Pub. No.: WO2019/208300
PCT Pub. Date: Oct. 31, 2019

(65) Prior Publication Data
US 2021/0228109 A1    Jul. 29, 2021

(30) Foreign Application Priority Data
Apr. 26, 2018 (JP) ................. 2018-085684

(51) Int. Cl.
*A61B 5/113* (2006.01)
*A61B 5/08* (2006.01)

(52) U.S. Cl.
CPC ............ *A61B 5/113* (2013.01); *A61B 5/0816* (2013.01)

(58) Field of Classification Search
None
See application file for complete search history.

(56) References Cited

U.S. PATENT DOCUMENTS 6,719,708 B1   4/2004  Jansen
7,168,429 B2   1/2007  Matthews et al.
(Continued)

FOREIGN PATENT DOCUMENTS

CN   107106085 A    8/2017
JP   61-024010 B    6/1986
(Continued)

OTHER PUBLICATIONS

English translation of the Written Opinion for corresponding International Application No. PCT/JP2019/016128 dated Jul. 9, 2019.
(Continued)

*Primary Examiner* — Jay B Shah
(74) *Attorney, Agent, or Firm* — Pearne & Gordon LLP (57) ABSTRACT

A biological state monitoring system (100) for monitoring a biological state of a subject on a bed (BD) over a predetermined monitoring period, includes: at least one load detector (11, 12, 13, 14) configured to detect a load of the subject on the bed; and a respiratory rate estimating unit (34) configured to successively obtain and output estimated values of a respiratory rate of the subject, based on a temporal variation of a detection value of the load detector. The monitoring period includes a body motion period in which the subject has a body motion, and a resting period in which the subject merely performs a respiration. In a case that the monitoring period shifts from a first resting period to the body motion period and then from the body motion period to a second resting period, the respiratory rate estimating unit outputs, in the body motion period and a predetermined period starting from the shifting from the body motion period to the second resting period, a last estimated value which is the latest (Continued)

among the estimated values obtained successively in the first resting period.

12 Claims, 8 Drawing Sheets

(56) References Cited

U.S. PATENT DOCUMENTS

| | | | |
|---|---|---|---|
| 2003/0236647 A1* | 12/2003 | Yoon | G01N 2/31 702/183 |
| 2005/0113711 A1 | 5/2005 | Nakatani et al. | |
| 2009/0221926 A1 | 9/2009 | Younes | |
| 2011/0066062 A1* | 3/2011 | Banet | A61B 5/1118 600/534 |
| 2011/0172551 A1* | 7/2011 | Al-Ali | A61B 5/08 600/529 |
| 2012/0116187 A1 | 5/2012 | Hayes et al. | |
| 2012/0132211 A1 | 5/2012 | Halperin et al. | |
| 2014/0088378 A1 | 3/2014 | Muzet | |
| 2015/0157258 A1 | 6/2015 | Beattie et al. | |
| 2017/0265815 A1* | 9/2017 | Katsuki | A61B 5/6891 |
| 2017/0273617 A1 | 9/2017 | Kaji | |
| 2017/0347948 A1 | 12/2017 | Thein et al. | |
| 2018/0146889 A1 | 5/2018 | Akatsu et al. | |
| 2018/0206793 A1 | 7/2018 | Akatsu et al. | |

FOREIGN PATENT DOCUMENTS

| | | |
|---|---|---|
| JP | 2006-280615 A | 10/2006 |
| JP | 2007-175225 A | 7/2007 |
| JP | 4002905 B2 | 11/2007 |
| JP | 4829020 B2 | 11/2011 |
| JP | 4883380 B2 | 2/2012 |
| JP | 2012-165979 A | 9/2012 |
| JP | 2014-516681 A | 7/2014 |
| JP | 6105703 B1 | 3/2017 |
| JP | 2017-064350 A | 4/2017 |
| JP | 2017-077451 A | 4/2017 |
| JP | 2017-104360 A | 6/2017 |
| WO | 2013/025922 A1 | 2/2013 |
| WO | 2017/018506 A1 | 2/2017 |
| WO | 2017/056476 A1 | 4/2017 |

OTHER PUBLICATIONS

International Search Report for corresponding International Application No. PCT/JP2019/016128 dated Jul. 9, 2019.
Written Opinion for corresponding International Application No. PCT/JP2019/016128 dated Jul. 9, 2019.
Notice of Reasons for Rejection for corresponding Japanese Application No. 2018-085684 dated Sep. 29, 2020 and English translation.
Chinese Office Action dated Apr. 13, 2021 for corresponding Chinese Application No. 201980028293.5 and English translation.
Related U.S. Appl. No. 17/050,511, filed Oct. 26, 2020.
International Search Report for related International Application No. PCT/JP2019/017162 dated Jul. 23, 2019 and English translation.
Written Opinion for related International Application No. PCT/JP2019/017162 dated Jul. 23, 2019 and English translation.
First Office Action dated Jan. 19, 2021 for related U.S. Appl. No. 17/050,511.
Notice of Allowance dated May 24, 2021 for related Chinese Application No. 201980028227.8 and English translation.
Extended European Search Report dated Jan. 4, 2022 for related European Application No. 19792071.3.
Holtzman et al., "Breathing Sensor Selection During Movement", 33rd Annual International Conference of the IEEE EMBS, Boston, MA, USA, pp. 381-384, Aug. 30-Sep. 3, 2011.
Extended European Search Report dated Apr. 19, 2022 for related European Application No. 19792860.9.
Extended European Search Report dated Feb. 24, 2023 for related European Application No. 19792860.9.

* cited by examiner

BIOLOGICAL STATE MONITORING SYSTEM

TECHNICAL FIELD

The present invention relates to a biological state monitoring system for monitoring a biological state of a (human) subject on a bed on the basis of detection value of a load detector.

BACKGROUND ART

For the sites of medical treatment and caregiving service, it is proposed to monitor a biological state (biological condition) of a subject on the basis of such a (body weight) load of the subject on a bed as detected by load detectors. In particular, for example, it is proposed to estimate a respiratory rate of the subject on the basis of the detected load.

Patent Literature 1 discloses that the subject's respiratory rate is detected by a frequency analysis of a measuring value of load sensors arranged under legs of a bed. Patent Literature 2 discloses that load detectors are arranged under legs of a bed to find a movement of the center of gravity of a biological subject under detection on a bed and, based on the movement of the center of gravity, a respiratory motion and heartbeats of the biological subject under detection is found.

CITATION LIST

Patent Literature 1: Japanese Patent No. 4883380
Patent Literature 2: Japanese Examined Patent Publication 61-24010

SUMMARY

Technical Problem

An object of the present invention is to provide a biological state monitoring system capable of outputting an estimated value of the respiratory rate of a subject with high reliability.

Solution to the Problem

According to a first aspect of the present invention, there is provided a biological state monitoring system for monitoring a biological state of a subject on a bed over a predetermined monitoring period, the system including:
at least one load detector configured to detect a load of the subject on the bed; and
a respiratory rate estimating unit configured to successively obtain and output estimated values of a respiratory rate of the subject, based on a temporal variation of a detection value of the load detector,
wherein the monitoring period includes a body motion period in which the subject has a body motion, and a resting period in which the subject merely performs a respiration, and
in a case that the monitoring period shifts from a first resting period to the body motion period and then from the body motion period to a second resting period, the respiratory rate estimating unit outputs, in the body motion period and a predetermined period starting from the shifting from the body motion period to the second resting period, a last estimated value which is the latest among the estimated values obtained successively in the first resting period.

The biological state monitoring system according to the first aspect may further include a body motion determining unit configured to determine whether or not the subject has the body motion based on the temporal variation of the detection value of the load detector.

In the biological state monitoring system according to the first aspect, the at least one load detector may be a plurality of load detectors each of which is configured to detect the load of the subject on the bed. Further, the biological state monitoring system according to the first aspect may further include a respiratory waveform obtaining unit configured to obtain a respiratory waveform of the subject based on the temporal variation of the detection value of each of the plurality of load detectors, and the respiratory rate estimating unit may be configured to obtain the estimated values of the respiratory rate of the subject based on the respiratory waveform.

In the biological state monitoring system according to the first aspect, the respiratory rate estimating unit may be configured to:
obtain an average of inter-peak distances of the respiratory waveform, of the subject, obtained within a predetermined sampling period, the inter-peak distance being a distance between two adjacent peaks of the respiratory waveform; and
obtain the estimated values of the respiratory rate of the subject by using the following equation, provided that $t_{AV}$ is the average of the inter-peak distances and R is the estimated value of the respiratory rate of the subject.

$$R=60/t_{AV}$$

In the biological state monitoring system according to the first aspect, the respiratory rate estimating unit may be configured to:
obtain, after the predetermined period in the second resting period has been ended, the inter-peak distance between first and second peaks of the respiratory waveform of the subject, the first and second peaks being firstly and secondly exhibited peaks in the second resting period, respectively; and
obtain and output the estimated value of the respiratory rate of the subject by using the following equation, provided that t is the inter-peak distance and R is the estimated value of the respiratory rate of the subject.

$$R=60/t_{AV}$$

In the biological state monitoring system according to the first aspect, a length of the predetermined period in the second resting period may be substantially equal to a length of the predetermined sampling period.

The biological state monitoring system according to the first aspect may further include a display unit configured to display the estimated values of the respiratory rate of the subject, outputted by the respiratory rate estimating unit.

According to a second aspect of the present invention, there is provided a bed system including:
a bed; and
the biological state monitoring system according to the first aspect.

The biological state monitoring system of the present invention is capable of outputting an estimated value of the respiratory rate of a subject with high reliability.

DESCRIPTION OF EMBODIMENT

Explanations will be made on a biological state (condition) monitoring system 100 according to an embodiment of the present invention (FIG. 1), with an example of using the system together with a bed BD (FIG. 2) to estimate a respiratory rate of a subject S on the bed BD.

Figure 1:
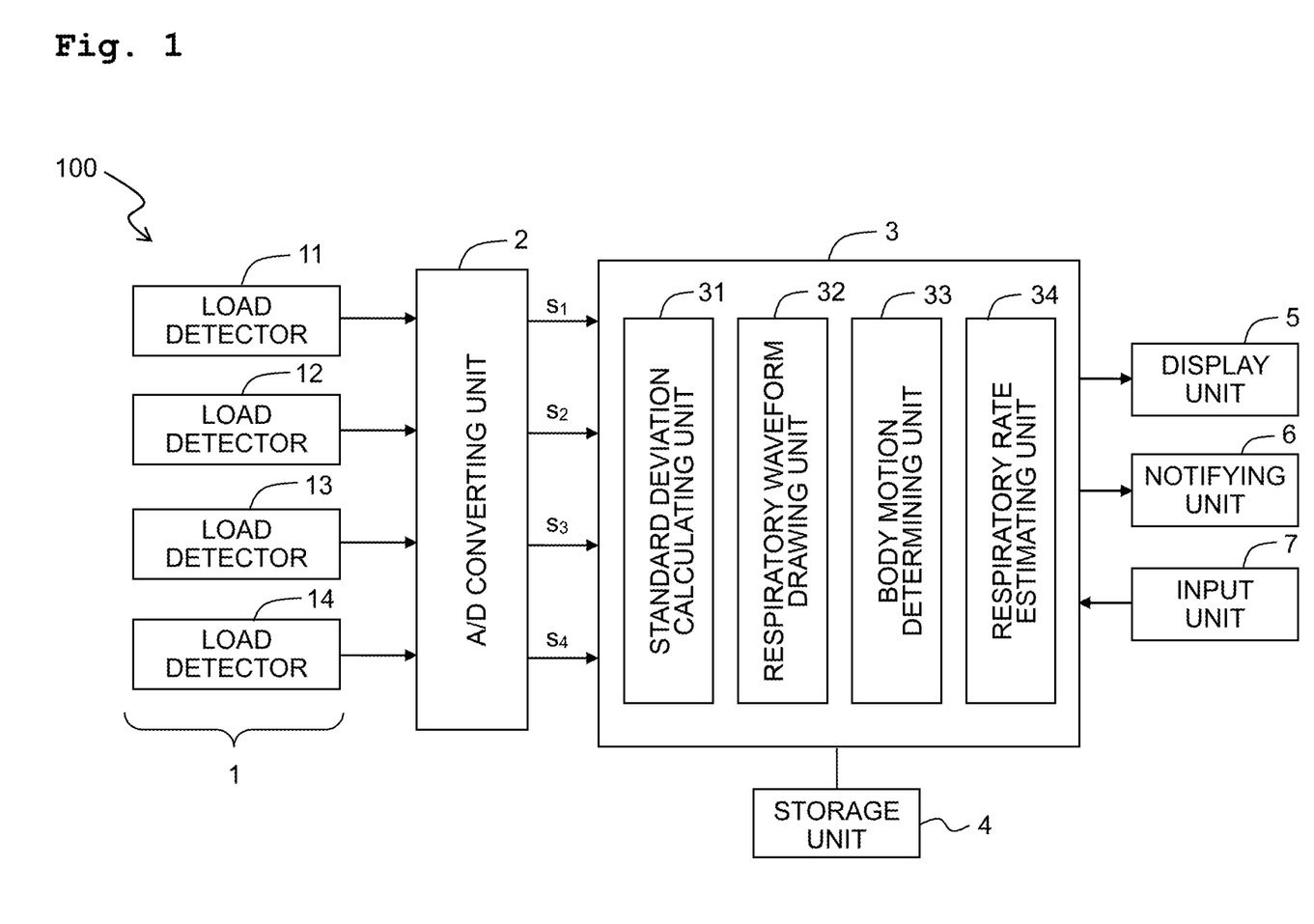
FIG. 1 is a block diagram depicting a configuration of a biological state monitoring system according to an embodiment of the present invention.

As depicted in FIG. 1, the biological state monitoring system 100 of the embodiment primarily has a load detecting unit 1, a control unit (controller) 3, and a storage unit 4. The load detecting unit 1 and the control unit 3 are connected via an A/D converting unit 2. The control unit 3 is further connected to a display unit 5, a notifying unit 6, and an input unit 7.

The load detecting unit 1 includes four load detectors 11, 12, 13, and 14. Each of the load detectors 11, 12, 13, and 14 is a load detector for detecting a load by using, for example, a beam-type load cell. Such a load detector is disclosed, for example, in Japanese Patent No. 4829020 and Japanese Patent No. 4002905. Each of the load detectors 11, 12, 13, and 14 is connected to the A/D converting unit 2 by way of wiring or wirelessly.

Figure 2:
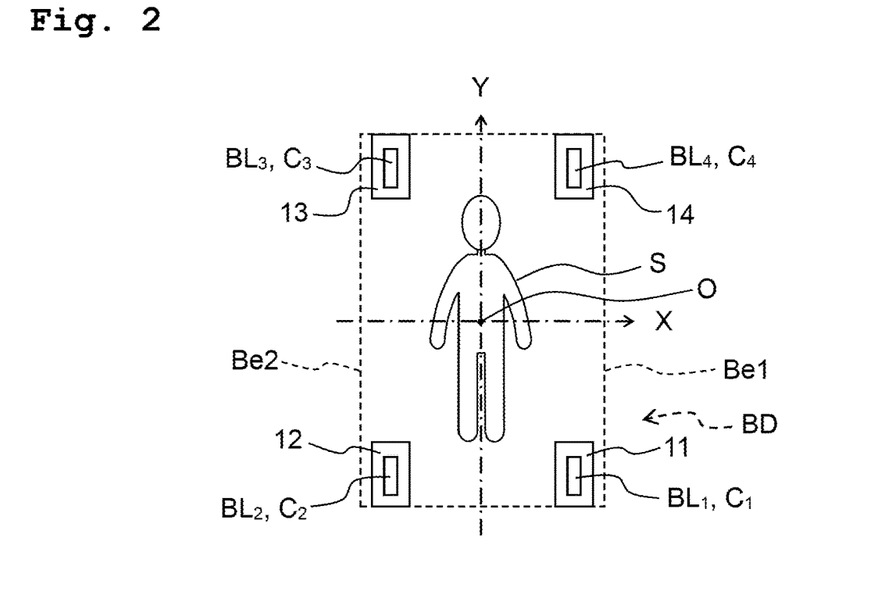
FIG. 2 is an illustrative view depicting an arrangement of load detectors for a bed.

As depicted in FIG. 2, the four load detectors 11 to 14 of the load detecting unit 1 are arranged respectively under casters $C_1$, $C_2$, $C_3$, and $C_4$ fitted on the lower ends of legs $BL_1$, $BL_2$, $BL_3$, and $BL_4$ at the four corners of the bed BD used by the subject S.

The A/D converting unit 2 includes an A/D convertor connected respectively to the load detecting unit 1 and the control unit 3 by way of wiring or wirelessly, to convert analog signals fed from the load detecting unit 1 to digital signals.

The control unit 3 is a dedicated or general-purpose computer inside which a standard deviation calculating unit 31, a respiratory waveform drawing unit 32 (respiratory waveform calculating unit; respiratory waveform obtaining (acquiring) unit), a body motion determining unit 33, and a respiratory rate estimating unit (respiratory rate determining unit; respiratory rate calculating unit) are constructed.

The storage unit 4 is a storage device for storing data used in the biological state monitoring system 100 and, for example, a hard disk (magnetic disk) can be used for that purpose.

The display unit 5 is monitor such as a liquid crystal monitor or the like for displaying information outputted from the control unit 3 to users of the biological state monitoring system 100.

The notifying unit 6 includes a device to auditorily perform a predetermined notification on the basis of the information fed from the control unit 3, such as a speaker, for example.

The input unit 7 is an interface for performing predetermined inputs for the control unit 3, which may be a keyboard and a mouse.

An explanation will be made on an operation of estimating (determining) the respiratory rate of the subject on the bed by using the biological state monitoring system 100 of such kind.

Figure 3:
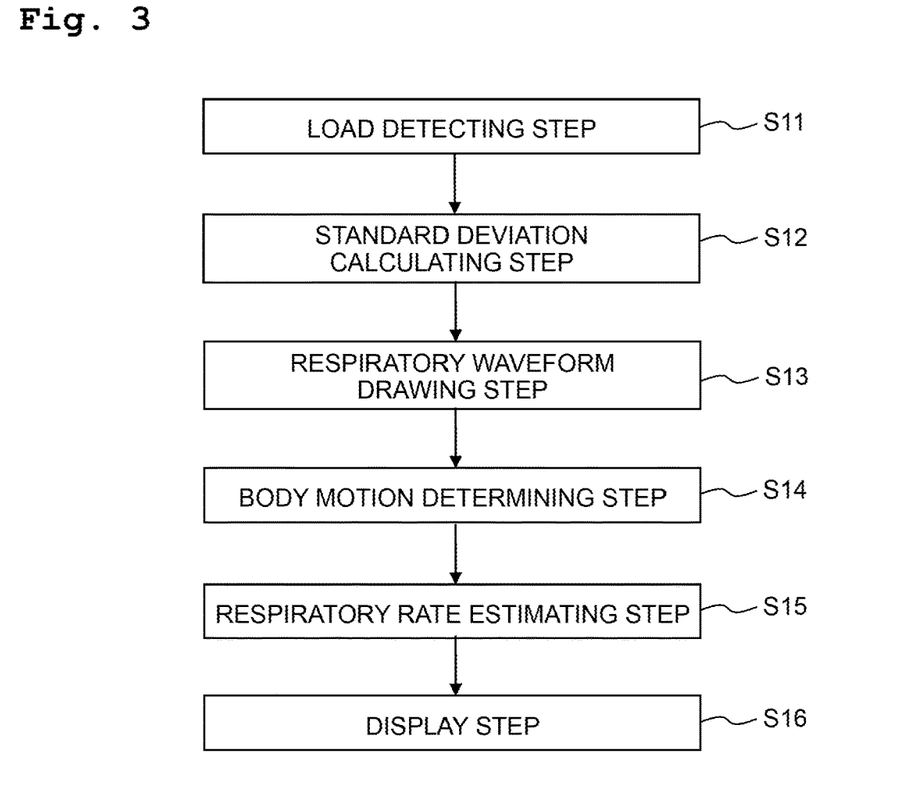
FIG. 3 is a flow chart depicting a method for estimating a respiratory rate by using the biological state monitoring system.

As depicted in the flow chart of FIG. 3, estimation of the respiratory rate of the subject performed by using the biological state monitoring system 100 includes a load detecting step S11 for detecting the load of a subject S, a standard deviation calculating step S12 for calculating a standard deviation showing the degree of variation of the detected load, a respiratory waveform drawing step S13 for drawing a respiratory waveform of the subject on the basis of the detected load, a body motion determining step S14 for determining the body motion of the subject by using the standard deviation found in the standard deviation calculating step S12, and the amplitude of the respiratory waveform drawn in the respiratory waveform drawing step S13, a respiratory rate estimating step S15 for estimating and outputting the respiratory rate of the subject on the basis of the respiratory waveform drawn in the respiratory waveform drawing step S13, and a display step S16 for displaying the outputted respiratory rate.

[The Load Detecting Step]

In the load detecting step S11, the load detectors 11, 12, 13, and 14 are used to detect the load of the subject S on the bed BD. The load of the subject S on the bed BD is applied dispersively to the load detectors 11 to 14 arranged respectively under the legs $BL_1$ to $BL_4$ of the bed BD at the four corners. The load of the subject S is detected dispersively by the four load detectors.

Each of the load detectors 11 to 14 detects the load (or variation of load), and outputs the result as an analog signal to the A/D converting unit 2. The A/D converting unit 2 converts the analog signal into a digital signal through a sampling period of 5 milliseconds, for example, and then outputs the digital signal (to be referred to below as "load signal") to the control unit 3. Hereinafter, the term "load signals $s_1$, $s_2$, $s_3$, and $s_4$" will be used to refer respectively to the load signals obtained in the A/D converting unit 2 by converting the analog signals outputted from the load detectors 11, 12, 13, and 14 into the digital format.

[The Standard Deviation Calculating Step]

In the standard deviation calculating step S12, the standard deviation calculating unit 31 calculates standard deviations $\sigma_1$, $\sigma_2$, $\sigma_3$, and $\sigma_4$ (moving standard deviations) of a sampling value included in a predetermined sampling period (5 seconds for example) for each of load signals $s_1$, $s_2$, $s_3$, and $s_4$. The calculation may be performed at any time (or continuously).

Figure 4:
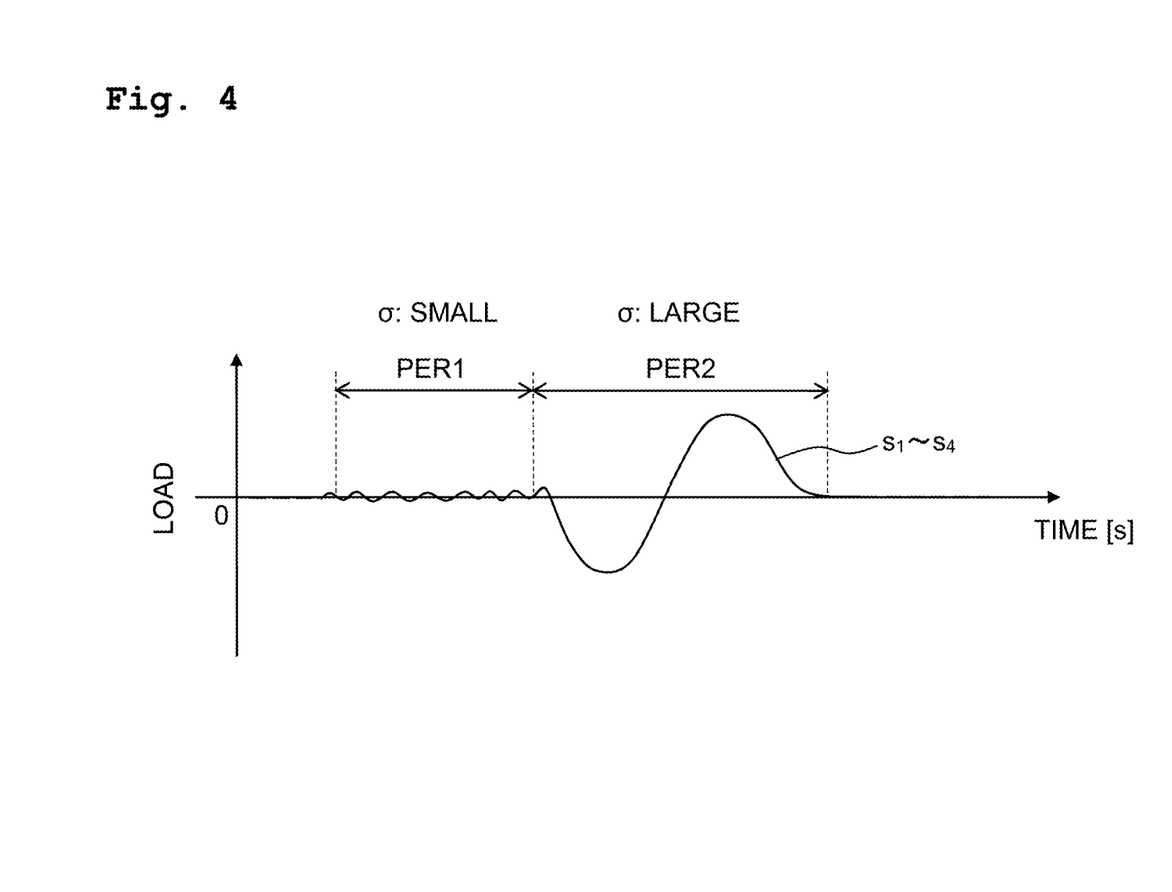
FIG. 4 is a schematic graph depicting an aspect of variation in load values detected by the load detectors in both a resting period when a subject only respires and a body motion period when the subject is performing a body motion.

The standard deviation denotes the magnitude of variation (dispersion) of the sampling value. Thus, as depicted in FIG. 4, the standard deviations $\sigma_1$ to $\sigma_4$ become small during a period PER1 in which the subject S is resting on the bed BD and there is a small magnitude of variation in the load signals $s_1$ to $s_4$. On the other hand, the standard deviations $\sigma_1$ to $\sigma_4$ become large during a period PER2 in which the subject S is moving his/her body (in which there is a body motion arising in the subject S) and there is a large magnitude of variation in the load signals $s_1$ to $s_4$.

Therefore, during a period when there is a body motion arising in the subject S, the standard deviations $\sigma_1$ to $\sigma_4$ have larger values in comparison to a period when there is no body motion arising in the subject S.

In the present specification and in the present invention, the term "body motion" refers to any motion of the subject's head, torso (trunk, body-trunk), and/or four limbs. The body motion does not include motions of internal organs, blood vessels and the like along with the respirations, heartbeats, and the like. As an example, the body motion can be classified into a large body motion along with the motion of the subject S in the torso (trunk, body-trunk), and a small body motion along with the motion of the subject only in the four limbs, the head, and/or the like. One example of the large body motion is turn-over, sit-up or get-up, or the like, whereas one example of the small body motion is, a motion of the hands, the feet, the head or the like during sleep. When heartbeats, respirations and body motions arise in the subject, the load signals $s_1$ to $s_4$ fed from the load detectors 11 to 14 vary accordingly. The magnitude of variation increases in the order of the variation due to the heartbeats of the subject S, the variation due to the respirations of the subject S, the variation due to the small body motion of the subject S, and the variation due to the large body motion of the subject S.

Note that in the determination of a body motion of the subject described in the present specification and in the present invention, the magnitude of variation in the load signals $s_1$ to $s_4$ due to the heartbeats of the subject S is so small as neglectable. Therefore, in the present specification and in the present invention, the term "the subject only (merely) respires (or the subject merely performs a respiration)", the load values and the load signals "vary due only to the respiration(s)", and the like are used to mean that the subject has no body motion, and the load values and the load signals show no variation due to the body motion, but not to mean that the subject does not have heartbeats, the load values and the load signals do not include the variation due to the heartbeats, etc.

[The Respiratory Waveform Drawing Step]

In the respiratory waveform drawing step S13, the respiratory waveform drawing unit 32 (respiratory waveform calculating unit; respiratory waveform obtaining(acquiring) unit) draws a respiratory waveform of the subject S on the basis of the load signals $s_1$ to $s_4$.

The respiration of human is performed by moving the chest and the diaphragm to expand and shrink the lungs. In this context, when the air is inhaled (or an inspiration is performed), i.e., when the lungs are expanded, the diaphragm is lowered downwardly, and the internal organs are also moved downwardly. On the other hand, when the air is expired (or an expiration is performed), i.e., when the lungs are shrunk, the diaphragm is raised upwardly, and the internal organs are also moved upwardly. As disclosed in the specification of Japanese Patent No. 6105703 granted to the present applicants, the center of gravity G (of the subject) moves slightly along with the movement of the internal organs, the moving direction thereof being approximately along the subject's backbone extending direction (body axis direction).

In the present specification and in the present invention, the term "respiratory waveform (respiration waveform)" refers to a waveform showing an aspect of the oscillation (vibration) of the subject's center of gravity oscillating (vibrating) in the subject's body axis direction due to the subject's respirations, by plotting the aspect on the temporal axis. One period of the respiratory waveform corresponds to one respiration of the subject (one inspiration and expiration). The amplitude of the respiratory waveform is affected by the subject's (physical) frame (build, physique) and/or respiratory depth. In particular, for example, if the subject has a large frame or the subject performs a deep respiration, then the amplitude becomes large, whereas if the subject has a small frame or the subject performs a shallow respiration, then the amplitude becomes small.

The respiratory waveform drawing unit 32 draws, in particular, the respiratory waveform in the following manner.

Figure 5:
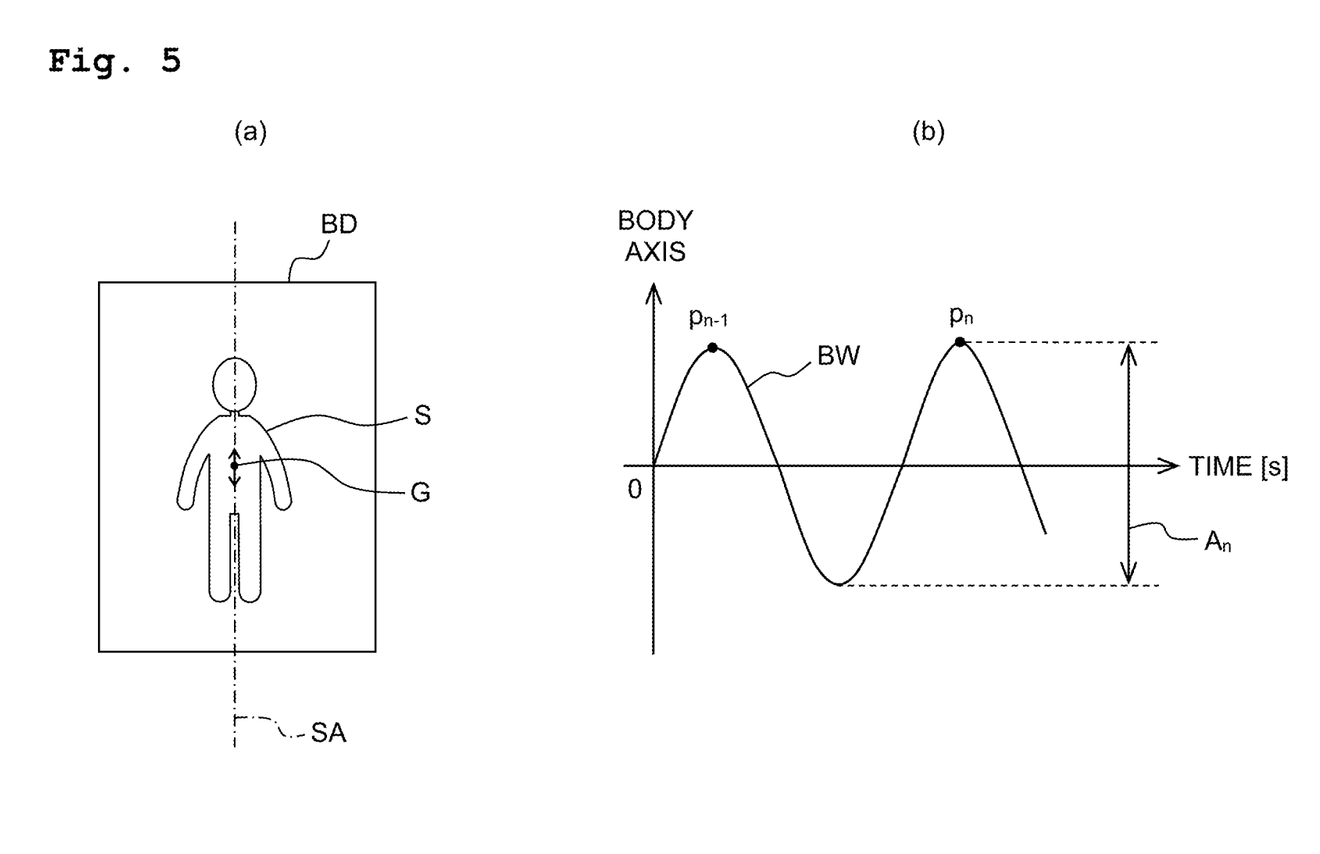
FIG. 5(a) is an illustrative view conceptually depicting an aspect where the center of gravity of the subject oscillates or vibrates in a body axis direction of the subject according to the respirations of the subject.
FIG. 5(b) is a graph depicting an example of a respiratory waveform drawn on the basis of the oscillation of the center of gravity of the subject according to the respirations of the subject.

First, the respiratory waveform drawing unit 32 calculates the position of the center of gravity G of the subject S at each sampling time on the basis of the load signals $s_1$ to $s_4$ fed from the load detecting unit 1. As depicted in FIG. 5(a), the center of gravity G of the subject S oscillates in the direction of the body axis SA of the subject S in accordance with or due to the respiration of the subject S.

Next, the respiratory waveform drawing unit 32 draws a respiratory waveform BW (FIG. 5(b)) by way of plotting, on the vertical axis of a graph, the distance between the positions obtained by projecting the position of the center of gravity G at each time on the body axis SA, and the oscillation center of oscillation of the center of gravity G according to the respiration. The direction of the vertical axis of the graph matches the direction of the body axis SA. The horizontal axis of the graph shows time.

Note that it is not necessary for the respiratory waveform drawing unit 32 to actually draw the respiratory waveform but it is possible to only obtain data indicating the respiratory waveform.

[The Body Motion Determining Step]

In the body motion determining step S14, the body motion determining unit 33 uses the standard deviations $\sigma_1$ to $\sigma_4$ calculated in the standard deviation calculating step S12 and the amplitude of the respiratory waveform BW drawn in the respiratory waveform drawing step S13, to determine whether or not there is a body motion arising in the subject S (whether or not the subject S has a body motion).

The determination is performed in the following manner in particular for example.

First, the body motion determining unit 33 detects the peaks for the respiratory waveform BW drawn in the respiratory waveform drawing step S13, and calculates the difference between the minimum value over the period between the latest peak $p_n$ and the previous peak $p_{n-1}$, and the latest peak $p_n$, as the latest amplitude $A_n$ of the respiratory waveform BW (FIG. 5(b)). Then, the body motion determining unit 33 finds an average amplitude $A_{AVn}$ which is a simple average (value) of the amplitude $A_n$ and the amplitudes $A_{n-1}$, $A_{n-2}$, ... which are calculated before the amplitude $A_n$. While an arbitrary number of amplitudes $A_n$ can be used for calculating the average amplitude $A_{AVn}$, as one example, the number may be such as obtained in a sampling period of 5 seconds or so.

Note that in order to confirm that the respiratory waveform BW, which is involved in calculating the amplitudes $A_n$, $A_{n-1}$, $A_{n-2}$, ... and the average amplitude $A_{AVn}$, is the respiratory waveform obtained from a resting period (during which the subject only respires (performs respirations) without body motion arising), (i.e., in order to confirm that there is no error included due to the movement of the center of gravity because of some body motion), a comparison may be made between a threshold value $\sigma_0$ and either a simple average $\sigma_{AV}$ of the standard deviations $\sigma_1$ to $\sigma_4$ or any one of the standard deviations $\sigma_{AV}$ to $\sigma_4$. The threshold value $\sigma_0$ is set at such a small value as able to reliably determine that there is no body motion arising in the subject S as long as the simple average $\sigma_{AV}$ or any one of the standard deviations $\sigma_1$ to $\sigma_4$ is smaller than that value (conversely, even if the simple average $\sigma_{AV}$ or any one of the standard deviations $\sigma_1$ to $\sigma_4$ is not smaller than that value, it is still possible that there is no body motion arising in the subject S).

Next, the body motion determining unit 33 finds normalized standard deviations $\sigma s_1$ to $\sigma s_4$ by the following Formula (Equation) 1.

$$\sigma s_m = \sigma_m / A_{AVn} (m=1,2,3,4) \qquad \text{(Formula 1)}$$

Then, the body motion determining unit 33 finds a simple average $\sigma s_{AV}$ of the calculated normalized standard deviations $\sigma s_1$ to $\sigma s_4$ and, based on a comparison between the simple average $\sigma s_{AV}$ and a predetermined threshold value $\sigma s_{TH}$, determines whether or not there is a body motion arising in the subject S (whether or not the subject S has a body motion). In particular, for example, if the simple average $\sigma s_{AV}$ is larger than or equal to the threshold value $\sigma s_{TH}$, then it is determined that there is a body motion arising in the subject S (the subject S has a body motion), whereas if the simple average $\sigma s_{AV}$ is smaller than the threshold value $\sigma s_{TH}$, then it is determined that there is no body motion arising in the subject S (the subject S has no body motion).

During a period when it is determined that there is no body motion arising in the subject S, the body motion determining unit 33 calculates the latest amplitude $A_n$ for each one period of the respiratory waveform BW on the basis of the respiratory waveform BW acquired by the respiratory waveform drawing unit 32. Then, using the average amplitude $A_{AVn}$ calculated anew by using the value of the calculated latest amplitude $A_n$, and the values of the standard deviations $\sigma_1$ to $\sigma_4$ calculated at each sampling time (as an example, every 5 milliseconds), the body motion determining unit 33 calculates, successively, the normalized standard deviations $\sigma s_1$ to $\sigma s_4$ by the Formula 1 and calculates the simple average $\sigma s_{AV}$.

Determining whether or not there is a body motion arising in the subject S is performed by the successive comparisons between the predetermined threshold value $\sigma s_{TH}$ and the simple average $\sigma s_{AV}$ calculated successively in the above manner.

After it is determined as a result of the determination that there is a body motion arising in the subject S, the body motion determining unit 33 ceases to update the average amplitude $A_{AVn}$ and continues to calculate the simple average $\sigma s_{AV}$ using the average amplitude $A_{AVn}$ having been calculated by this point. Then, based on a comparison between the calculated simple average $\sigma s_{AV}$ and the threshold value $\sigma s_{TH}$, the body motion determining unit 33 continues to determine whether or not there is a body motion arising in the subject S. This is because during a period when there is a body motion arising in the subject S, the amplitude and period of the respiratory waveform BW vary greatly due to the influence of the body motion, and thereby it is difficult to calculate a new amplitude $A_n$ and the average amplitude $A_{AVn}$ without error.

Next, if it is determined again that there is no body motion arising in the subject S, then based on the respiratory waveform BW acquired by the respiratory waveform drawing unit 32, the body motion determining unit 33 calculates the value of the latest amplitude $A_n$ and, using the same, calculates the average amplitude $A_{AVn}$ anew. Then, the body motion determining unit 33 calculates the simple average $\sigma s_{AV}$ using the latest average amplitude $A_{AVn}$ and, based on a comparison between the calculated simple average $\sigma s_{AV}$ and the predetermined threshold value $\sigma s_{TH}$, the body motion determining unit 33 continues to determine whether or not there is a body motion arising in the subject S.

Figure 6:
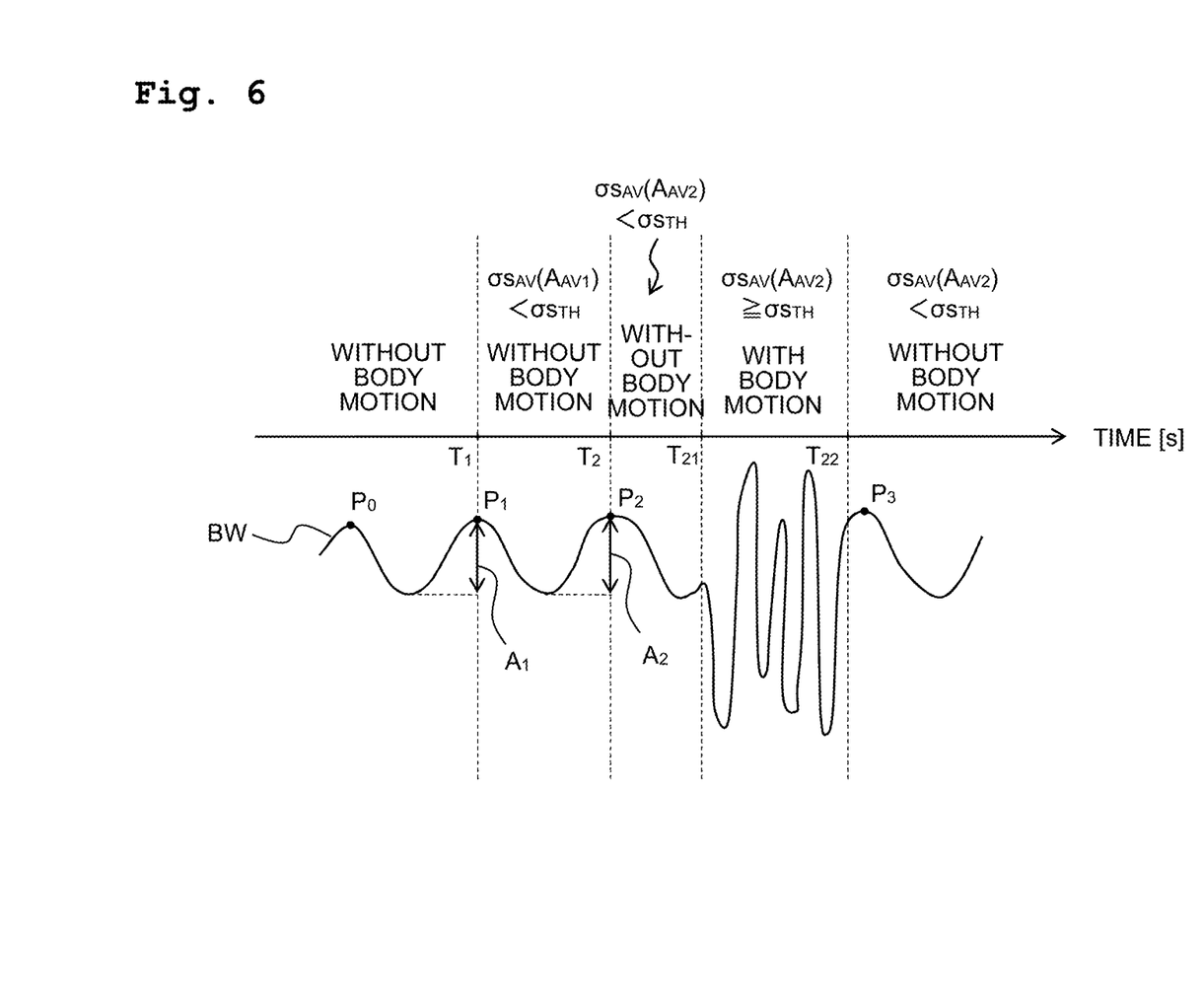
FIG. 6 is an illustrative view for explaining an example of specific method for determining the body motion with a body motion determining unit.

Referring to FIG. 6, a particular example of this step will be explained.

As depicted in FIG. 6, if a peak $P_1$ of the respiratory waveform BW and the latest amplitude $A_1$ are obtained at the time $T_1$, then for the period from the time $T_1$, the body motion determining unit 33 uses the average amplitude $A_{AV1}$ which is the simple average of the amplitude $A_1$ and the amplitudes $A_0$, $A_{-1}$, ... (all not shown) obtained right therebefore, to calculate successively the normalized standard deviations $\sigma s_1$ to $\sigma s_4$ and the simple average $\sigma s_{AV}$ (to be referred to here as $\sigma s_{AV}(A_{AV1})$); and determines whether or not there is a body motion arising in the subject S, based on a comparison between the simple average $\sigma s_{AV}(A_{AV1})$ and the threshold value $\sigma s_{TH}$.

Next, if another peak $P_2$ of the respiratory waveform BW and the latest amplitude $A_2$ are obtained at the time $T_2$, then for the period from the time $T_2$, the body motion determining unit 33 uses the average amplitude $A_{AV2}$ calculated by using the amplitude $A_2$, to calculate successively the normalized standard deviations $\sigma s_1$ to $\sigma s_4$ and the simple average $\sigma s_{AV}$ (to be referred to here as $\sigma s_{AV}(A_{AV2})$); and determines whether or not there is a body motion arising in the subject S, based on the comparison between the simple average $\sigma s_{AV}(A_{AV2})$ and the threshold value $\sigma s_{TH}$.

At the time $T_{21}$, if there is a body motion arising in the subject S, then the body motion determining unit 33 determines that there is a body motion arising in the subject S on the basis of the simple average $\sigma s_{AV}(A_{AV2})$ being equal to or larger than the threshold value $\sigma s_{TH}$. Then, after that, for the period when the simple average $\sigma s_{AV}(A_{AV2})$ is equal to or larger than the threshold value $\sigma s_{TH}$, the body motion determining unit 33 continues to determine the body motion using the simple average $\sigma s_{AV}(A_{AV2})$.

At the time $T_{22}$, if the body motion has come to an end in the subject S, then the body motion determining unit 33 determines that there is no body motion arising in the subject S on the basis of the simple average $\sigma s_{AV}(A_{AV2})$ being smaller than the threshold value $\sigma s_{TH}$. After that, the body motion determining unit 33 continues to determine the body motion using the simple average $\sigma s_{AV}(A_{AV2})$ until the latest amplitude $A_n$ of the respiratory waveform BW is obtained and the latest average amplitude $A_{AVn}$ is calculated again.

The body motion determining unit 33 uses the amplitude $A_n$ (average amplitude $A_{AVn}$) of the respiratory waveform to normalize the values of the standard deviations $\sigma_1$ to $\sigma_4$. The reason therefor is as follows.

As described above, generally speaking, the values of the standard deviations $\sigma_1$ to $\sigma_4$ become larger during a period when there is a body motion arising in the subject S. Therefore, it is conceivable to determine whether or not there is a body motion arising in the subject S by way of comparison between the values of the standard deviations $\sigma_1$ to $\sigma_4$ and a predetermined threshold value.

However, according to the discovery and knowledge of the present inventors, for a subject who has a large frame, the values of the standard deviations $\sigma_1$ to $\sigma_4$ may still be comparatively large even during a period of only performing respirations without the body motion because the movement of his/her internal organs due to the respirations is also large. Further, even for a subject who does not have a large frame, the values may still become large if, for example, the subject performs a deep respiration. Hence, if the body motion determination is performed by comparing the values of the standard deviations $\sigma_1$ to $\sigma_4$ to a predetermined threshold value, in such a case, even though there is no body motion arising in the subject, a mistaken determination may be made to give the incorrect result that there is a body motion arising in the subject.

On the other hand, if the respiratory waveform is focused on, then as described earlier on, the amplitude of the respiratory waveform is affected by the subject's frame and/or respiratory depth; therefore, if the subject has a large frame or the subject performs a deep respiration, then the amplitude becomes large, whereas if the subject has a small frame or the subject performs a shallow respiration, then the amplitude becomes small.

That is, by dividing the values of the standard deviations $\sigma_1$ to $\sigma_4$ by the average amplitude $A_{AVn}$ of the respiratory waveform BW to perform the normalization, it is possible to reduce (compensate; correct) the influence on the values of the standard deviations $\sigma_1$ to $\sigma_4$, exerted by the subject's frame and/or respiratory depth. Then, by using the normalized standard deviations $\sigma s_1$ to $\sigma s_4$ obtained through such normalization to determine the body motion, it is possible to raise the precision of determining the body motion.

[The Respiratory Rate Estimating Step]

In the respiratory rate estimating step S15, the respiratory rate estimating unit 34 (the respiratory rate determining unit) estimates (determines) the respiratory rate of the subject S on the basis of the respiratory waveform BW of the subject S drawn in the respiratory waveform drawing step S13, and outputs the estimated (determined) respiratory rate to the display unit 5.

In particular, the respiratory rate estimating unit 34 estimates the respiratory rate on the basis of the respiratory waveform BW by the following method.

The respiratory rate estimating unit 34 detects peaks in predetermined periods for the respiratory waveform BW drawn in the respiratory waveform drawing step S13. Then, when a new peak is detected, the respiratory rate estimating unit 34 finds distances (to be referred to below as inter-peak distances t) between any two adjacent peaks of the plurality of peaks included between a first time point at which the new peak is detected and a second time point before (preceding) the first time point by a predetermined time period (25 seconds for example; to be referred to below as "sampling time period for estimation" as appropriate).

Figure 7:
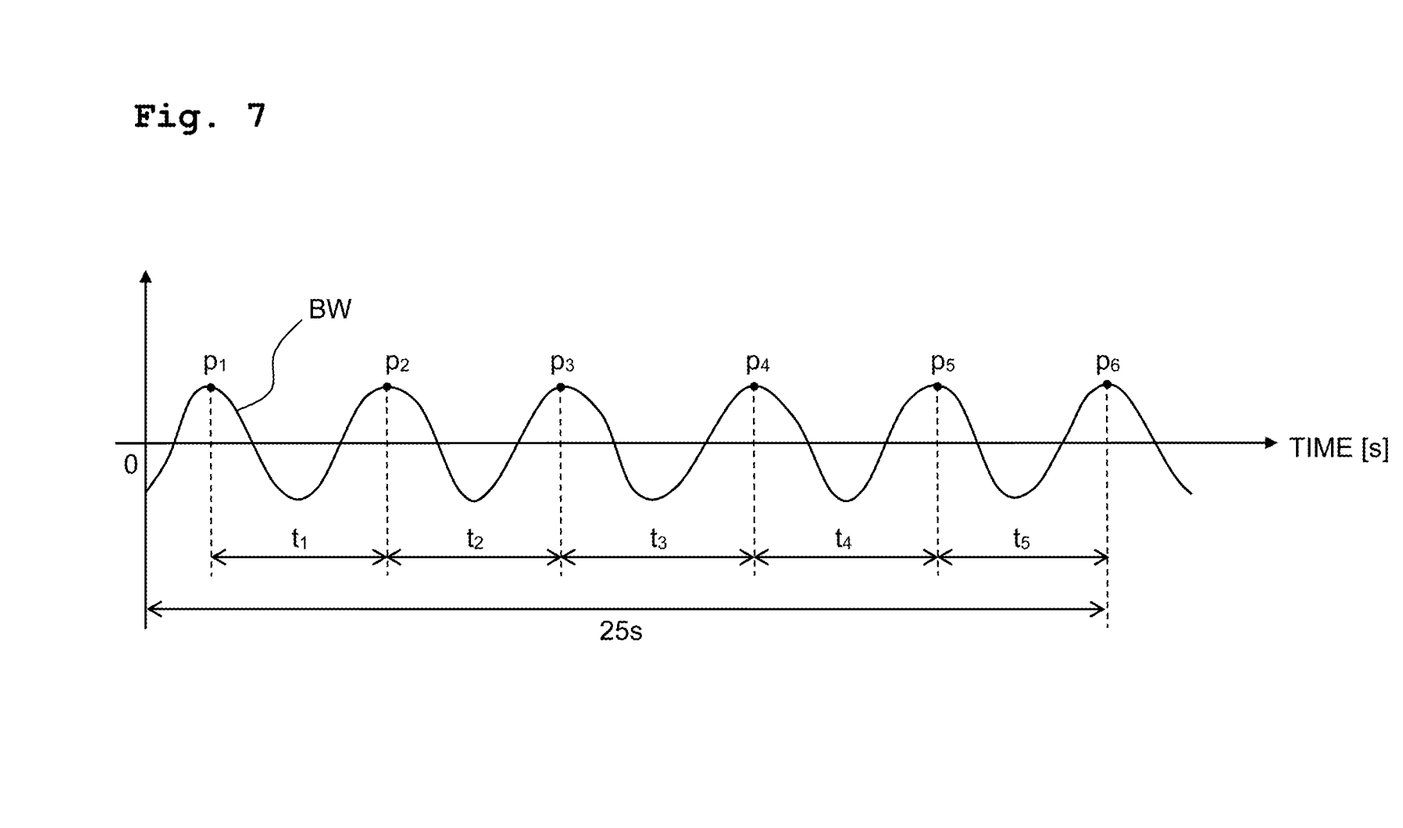
FIG. 7 is an illustrative view for explaining an exemplary method for estimating the respiratory rate of the subject on the basis of the respiratory waveform.

FIG. 7 depicts one example of the respiratory waveform BW included in the sampling time period for estimation over 25 seconds with peaks $p_1$ to $p_6$ of the respiratory waveform BW, and inter-peak distances $t_1$ to $t_5$ between the peaks $p_1$ to $p_6$.

Next, the respiratory rate estimating unit 34 finds an average value $t_{AV}$ of the plurality of inter-peak distances t by the following Formula 2.

$$t_{AV} = \frac{1}{N-1}\sum_{n=1}^{N-1} t_n \quad \text{(Formula 2)}$$

Herein, N is the number of peaks of the respiratory waveform BW included in the sampling time period for estimation. The average value $t_{AV}$ approximately corresponds to the average value of the respiratory periods of the subject S during the sampling time period for estimation.

Thereafter, the respiratory rate estimating unit 34 calculates an estimated value R of the respiratory rate over one minute of the subject S by the following Formula 3. Then, the calculated estimated value R is outputted to the display unit 5 as the estimated respiratory rate.

$$R = 60/t_{AV} \quad \text{(Formula 3)}$$

Further, the respiratory rate estimating unit 34 of this embodiment adjusts the value of the respiratory rate for output according to whether or not the subject S has a body motion. This adjustment will be explained as follows.

The respiratory rate estimating unit 34 successively calculates the estimated value R of the respiratory rate by using the Formulas 2 and 3 according to the above method whenever a peak of the respiratory waveform BW is detected both in a period (resting period) when the body motion determining unit 33 determines that the subject S does not have a body motion and in a period (body motion period) when the body motion determining unit 33 determines that the subject S has a body motion.

Then, in the resting period (excluding a predetermined period after the transition (shifting) from the body motion period to the resting period, as will be described later on), the calculated estimated values R are outputted successively to the display unit 5 as the estimated respiratory rates.

On the other hand, in the body motion period, the respiratory rate estimating unit 34 outputs the estimated value R calculated right before the transition (shifting) from the resting period to the body motion period, that is, the estimated value R calculated last in the resting period right therebefore, instead of the estimated value R of the respiratory rate calculated successively by using the Formulas 2 and 3 according to the above method, to the display unit 5 as the estimated respiratory rate.

Further, when a transition from a first resting period to a body motion period occurred and then a transition from the body motion period to a second resting period occurred, in a predetermined period after the transition from the body motion period to the second resting period, the respiratory rate estimating unit 34 outputs the value outputted in the preceding body motion period, that is, the estimated value R calculated right before the transition from the first resting period to the body motion period, to the display unit 5 as the estimated respiratory rate, instead of the estimated value R of the respiratory rate calculated successively by using the Formulas 2 and 3 according to the above method.

Then, after detecting two peaks of the respiratory waveform BW in the second resting period, the respiratory rate estimating unit 34 finds (obtains) the inter-peak distance t between those two peaks, and uses the value of the inter-peak distance t as the value of the average value $t_{AV}$ to calculate the estimated value R of the respiratory rate by the Formula 3. Then, the respiratory rate estimating unit 34 outputs the estimated value R calculated anew to the display unit 5 as the estimated respiratory rate, instead of the value outputted fixedly in the body motion period and the following predetermined period, that is, the estimated value R calculated right before the transition from the first resting period to the body motion period.

In the same manner, at the time points at which three and four peaks of the respiratory waveform BW have been detected, the respiratory rate estimating unit 34 obtains the inter-peak distances t between two adjacent peaks of the three and four peaks, respectively, to calculate the estimated value R of the respiratory rate by the Formula 3 by using a simple average (value) of those obtained inter-peak distances t as the value of the average value $t_{AV}$. Then, the respiratory rate estimating unit 34 outputs the calculated values as the estimated respiratory rate to the display unit 5. Then, after the sampling time period for estimation (25 seconds for here) has elapsed after (since) the transition from the body motion period to the second resting period, the respiratory rate estimating unit 34 restarts calculating the average value $t_{AV}$ by using the above Formula 2 to calculate the estimated value R by applying the calculated average value $t_{AV}$ to the above Formula 3, and output the calculated value to the display unit 5 as the estimated respiratory rate.

A specific example of this step will be explained, using FIG. 8.

Figure 8:
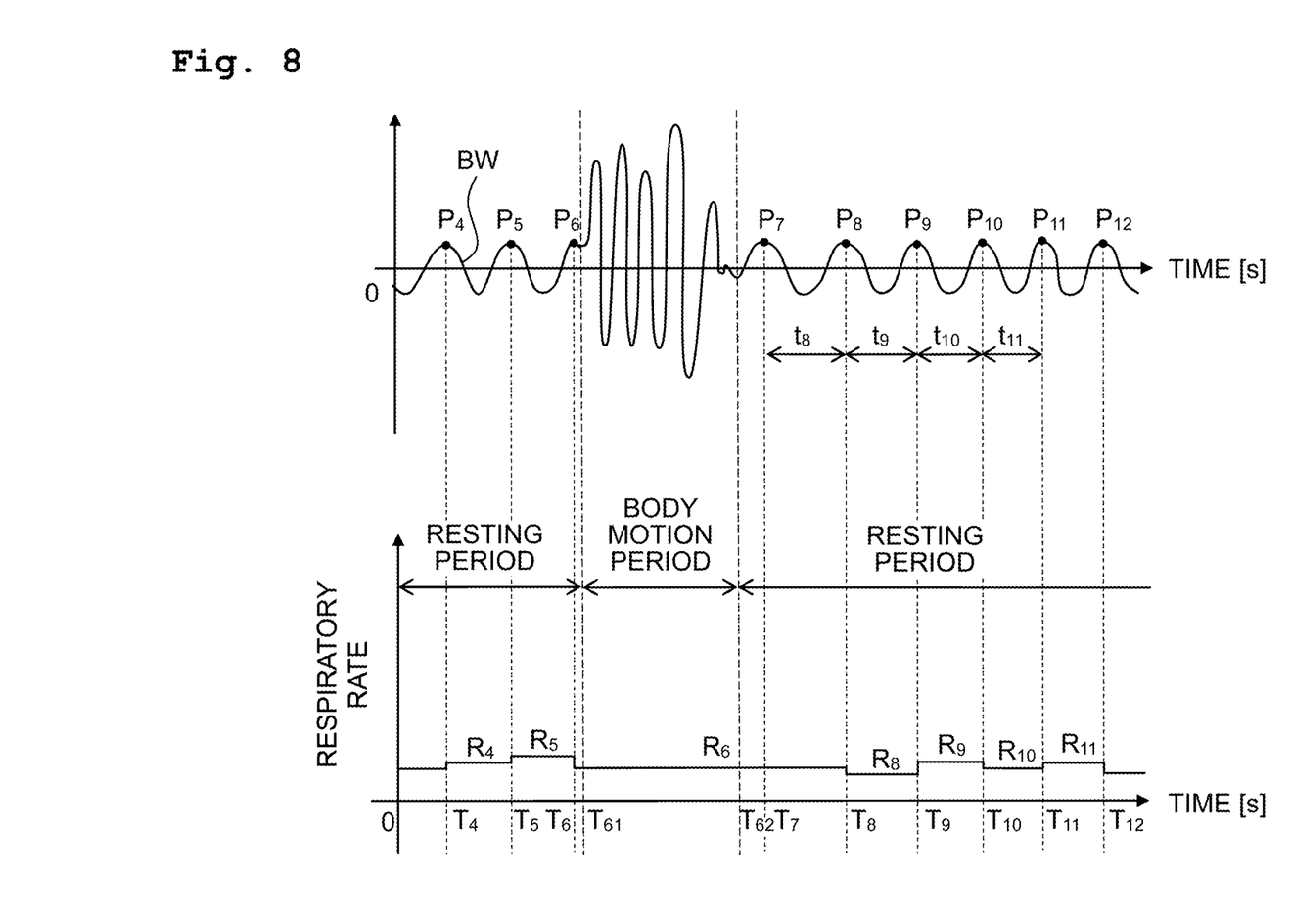
FIG. 8 is an illustrative view for explaining a specific example of a respiratory rate estimating step performed by a respiratory rate estimating unit.

As depicted in FIG. 8, after detecting the peak $P_4$ of the respiratory waveform BW at the time $T_4$ included in the resting period, the respiratory rate estimating unit 34 calculates the estimated value R of the respiratory rate by the above Formulas 2 and 3, on the basis of the respiratory waveform BW found in the sampling time period for estimation over 25 seconds with the time $T_4$ as the terminal, and outputs the calculated value as the estimated respiratory rate. Here, suppose that the respiratory rate $R_4$ is outputted. In the same manner, after detecting the peaks $P_5$ and $P_6$ of the respiratory waveform BW at the times $T_5$ and $T_6$, the respiratory rate estimating unit 34 calculates the estimated values R of the respiratory rate by the above Formulas 2 and 3, on the basis of the respiratory waveform BW found in the sampling time period for estimation with the times $T_5$ and $T_6$ as the terminals, and outputs the calculated values as the estimated respiratory rates. Here, suppose that the respiratory rates $R_5$ and $R_6$ are outputted.

Next, if a body motion arises in the subject S at the time $T_{61}$, then the respiratory rate estimating unit 34 switches the estimated value of the respiratory rate for output from the estimated value R calculated anew by using the above Formulas 2 and 3 to the estimated value calculated right before the time $T_{61}$ (equal to the respiratory rate $R_6$), on the basis of the body motion determining unit 33 having determined that the subject S has a body motion. Then, during the period when the body motion determining unit 33 determines that the body motion is arising in the subject S (the subject S has the body motion), that is, during the body motion period, the respiratory rate estimating unit 34 keeps outputting the respiratory rate $R_6$ as the estimated respiratory rate.

Further, after the body motion of the subject S comes to an end at the time $T_{62}$ such that the body motion determining unit 33 determines that there is no body motion arising in the subject S (that is, after returning to a resting period), the respiratory rate estimating unit 34 also keeps outputting the estimated value calculated right before the time $T_{61}$ (equal to the respiratory rate $R_6$) as the estimated respiratory rate, through a predetermined period, instead of the estimated value R calculated anew by using the above Formulas 2 and 3.

Then, after detecting the second peak $P_8$ after the body motion of the subject S comes to an end at the time $T_8$, the respiratory rate estimating unit 34 finds the inter-peak distance $t_8$ between the first peak $P_7$ and the peak $P_8$ after the body motion of the subject S comes to the end. Then, using the inter-peak distance $t_8$ as the average value $t_{AV}$, the respiratory rate estimating unit 34 calculates the estimated value R of the respiratory rate by the Formula 3, and outputs the newly calculated estimated value R as the estimated respiratory rate instead of the value outputted fixedly after the time $T_{61}$ (the respiratory rate $R_6$). Here, suppose that the respiratory rate $R_8$ is outputted.

After detecting the third peak $P_9$ after the body motion of the subject S comes to an end at the time $T_9$, the respiratory rate estimating unit 34 finds the inter-peak distance $t_9$ between the second peak $P_8$ and the peak $P_9$ after the body motion of the subject S comes to the end. Then, using a simple average of the inter-peak distance $t_8$ and the inter-peak distance $t_9$ as the average value $t_{AV}$, the respiratory rate estimating unit 34 calculates the estimated value R of the respiratory rate by the Formula 3, and outputs the calculated value as the estimated respiratory rate. Here, suppose that the respiratory rate $R_9$ is outputted.

In the same manner, after detecting the fourth peak $P_{10}$ and the fifth peak $P_{11}$ after the body motion of the subject S comes to an end at the times $T_{10}$ and $T_{11}$, the respiratory rate estimating unit 34 finds the inter-peak distance $t_{10}$ between the peak $P_9$ and the peak $P_{10}$, and the inter-peak distance $t_{11}$ between the peak $P_{10}$ and the peak $P_{11}$. Then, using the simple average of what has already been obtained in the inter-peak distances $t_8$ to $t_{11}$ as the average value $t_{AV}$, it calculates the estimated value R of the respiratory rate by the Formula 3, and outputs the calculated value as the estimated respiratory rate. Here, suppose that the respiratory rates $R_{10}$ and $R_{11}$ are outputted.

Then, after 25 seconds, which corresponds to the sampling time period for estimation, has elapsed since the time $T_{62}$, the respiratory rate estimating unit 34 restarts calculating the average value $t_{AV}$ by using the above Formula 2, to calculate the estimated value R of the respiratory rate by applying the calculated average value $t_{AV}$ to the above Formula 3. Then, it outputs the calculated value to the display unit 5 as the estimated respiratory rate.

The following statement is the reason why the respiratory rate estimating unit 34 outputs the estimated value R of the respiratory rate, calculated right before the transition from the resting period to the body motion period, as the estimated value of the respiratory rate of the subject S instead of the estimated value R calculated, in the body motion period and the predetermined initial period of the following resting period.

As depicted in FIG. 8, there are detected peaks in the respiratory waveform BW during the body motion period, too. However, as seen in the waveform depicted in FIG. 8, the respiratory waveform BW is affected and disturbed by the body motion of the subject S whereby the period of the respiratory waveform BW is also varying. Therefore, the inter-peak distances found on the basis of the peaks of the respiratory waveform BW in the body motion period do not reflect the respiratory period by their values. If the sampling time period for estimation includes a body motion period, then the average value $t_{AV}$ found by the Formula 2 is affected by the inter-peak distances which do not reflect the respiratory period in this manner. Therefore, there is also a high possibility for the estimated value R of the respiratory rate calculated by using the Formula 3 to deviate from the actual respiratory rate of the subject.

Therefore, in the body motion period and the predetermined initial period in the resting period following the body motion period, during which the body motion period is included inevitably in the sampling time period for estimation, the respiratory rate estimating unit 34 outputs the estimated value R calculated right before the transition from the resting period to the body motion period as the estimated value for those periods, instead of the estimated value R calculated anew. By virtue of this, reliability is maintained for the estimated value of the respiratory rate to offer the user of the biological state monitoring system 100.

Note that the respiratory rate estimating unit 34 may cease to detect the peaks of the respiratory waveform BW, cease to calculate the inter-peak distances, and cease to calculate the estimated values R using the Formulas 2 and 3, during the body motion period and during the predetermined period after the transition from the body motion period to the resting period.

In this embodiment, at the time point by which two peaks of the respiratory waveform BW of the resting period have been detected, the estimated value R is calculated by using the inter-peak distance between those peaks, and the calculated value is outputted. According to this method, after the transition from the body motion period to the resting period, it is possible to restart calculating and outputting the estimated value R of the respiratory rate with exclusion of the influence of disturbance of the respiratory waveform BW in the body motion period, without waiting for the passage of the time equivalent to the sampling time period for estimation. However, after an end of the body motion, it is allowable to keep outputting the estimated value R calculated right before the transition to the body motion period, until the lapse of the time almost equal to the sampling time period for estimation.

[The Display Step]

In the display step S16, the control unit 3 causes the display unit 5 to display the respiratory rate (estimated value) of the subject S outputted in the respiratory rate estimating step S15. Further, in the display step S16, the notifying unit 6 may be used to perform a notification in addition to or instead of the display using the display unit 5. In this case, for example, when the respiratory rate of the subject S reaches a predetermined set value, a notification sound may be emitted to notify the nurses, caregivers and/or others who are the users of the biological state monitoring system 100.

The effects of the biological state monitoring system 100 according to this embodiment are summarized as follows.

In a case that the subject S has a body motion, then the respiratory rate estimating unit 34 included in the biological state monitoring system 100 of this embodiment outputs the estimated value calculated right before an occurrence of the body motion, during a period in which the body motion is kept and during a predetermined period succeeding an end of the body motion, as the estimated value of the respiratory rate for those period. Therefore, even when the subject S has a body motion, it is possible for the biological state monitoring system 100 of this embodiment to suppress the influence of the body motion, thereby outputting the estimated value of the respiratory rate of the subject S with high reliability.

The respiratory rate estimating unit 34 included in the biological state monitoring system 100 of this embodiment restarts, at the point of detecting two peaks of the respiratory waveform BW after the transition from the body motion period to the resting period, calculating the estimated value of the respiratory rate by using the inter-peak distance between those peaks. Therefore, it is possible for the biological state monitoring system 100 of this embodiment to release the respiratory rate displayed on the display unit 5 from the state fixed at the value estimated right before a body motion, at an earlier timing after the end of the body motion.

The biological state monitoring system 100 of this embodiment uses the load detectors 11 to 14 arranged under the legs $BL_1$ to $BL_4$ of the bed BD to determine whether or not the subject S has a body motion. Therefore, it is not necessary to attach any measuring device to the body of the subject S so that the subject S will not feel discomfort and a sense of incongruity.

Modified Embodiments

It is also possible for the biological state monitoring system 100 of the above embodiment to adopt the following modified embodiments.

In the biological state monitoring system 100 of the above embodiment, the respiratory rate estimating unit 34 may estimate the respiratory rate of the subject S without using the respiratory waveform BW.

In particular, for example, the respiratory rate estimating unit 34 calculates the respiratory rate of the subject S by carrying out the Fourier analysis on at least one of the load signals $s_1$ to $s_4$ corresponding to the predetermined sampling period so as to specify the peak frequency coming up in the frequency band corresponding to the respirations (from about 0.2 Hz to about 0.33 Hz because the human respiration is performed about 12 to 20 times per minute). With the specified peak frequency, it is possible to calculate (estimate) the respiratory rate of the subject S over that period.

In this case, too, if the sampling period includes a body motion period, then the reliability of the calculated respiratory rate (estimated value) of the subject S may decrease due to a variation of the load signals $s_1$ to $s_4$ arising from the body motion. Therefore, it is possible to raise the reliability of the estimated value of the respiratory rate by adjusting the outputted value by the same method as used by the respiratory rate estimating unit 34 of the above embodiment.

In the biological state monitoring system 100 of the above embodiment, the body motion determining unit 33 normalizes the standard deviations $\sigma_1$ to $\sigma_4$ by dividing the standard deviations $\sigma_1$ to $\sigma_4$ by the average amplitude $A_{AVn}$ to reduce (compensate; correct) the influence on the values of the standard deviations $\sigma_1$ to $\sigma_4$, exerted by the frame and/or respiratory depth of the subject S. However, the compensating (correcting) method by utilizing the amplitude of the respiratory waveform BW is not limited to that. In particular, for example, the standard deviations $\sigma_1$ to $\sigma_4$ may be normalized by way of dividing the same by the latest amplitude $A_n$ of the respiratory waveform BW.

Note that, it is also possible to compensate the threshold value by using the amplitude of the respiratory waveform BW and compare the standard deviations $\sigma_1$ to $\sigma_4$ to the compensated threshold value, instead of compensating the standard deviations $\sigma_1$ to $\sigma_4$ by using the amplitude of the respiratory waveform BW and then comparing the compensated values to the threshold value. In particular, for example, in the above embodiment, instead of dividing the standard deviations $\sigma_1$ to $\sigma_4$ by the average amplitude $A_{AVn}$, it is possible to perform a desired compensation (correction) by multiplying the predetermined threshold value by the average amplitude $A_{AVn}$. In this manner, the two methods mentioned above are practically equivalent and thus it is possible to appropriately select either the standard deviations or the threshold value used in the comparison for the compensation (correction) by the amplitude of the respiratory waveform. In the present specification and in the present invention, the expression "compensating the standard deviations by the amplitude of the respiratory waveform" is termed to include compensating the threshold value by the amplitude of the respiratory waveform.

In the biological state monitoring system 100 of the above embodiment, the body motion determining unit 33 performs the body motion determination by the comparison between the simple average $\sigma s_{AV}$ of the normalized standard deviations $\sigma s_1$ to $\sigma s_4$ and the threshold value $\sigma s_{TH}$. However, it is also possible to determine the body motion by a comparison between at least one of the normalized standard deviations $\sigma s_1$ to $\sigma s_4$ and the threshold value, a comparison between simple average values of at least two or more of the normalized standard deviations $\sigma s_1$ to $\sigma s_4$ and the threshold value, a comparison between the total value of at least two or more of the normalized standard deviations $\sigma s_1$ to $\sigma s_4$ and the threshold value, or the like.

Further, in the biological state monitoring system 100 of the above embodiment, it is also capable for the body motion determining unit 33 to use a variance which is the squared standard deviation instead of the standard deviation. If the variance is normalized by the amplitude of the respiratory waveform, then the variance may be divided by the squared amplitude of the respiratory waveform. Therefore, in the present specification and in the present invention, the standard deviation is termed to include the variance.

The body motion determining unit 33 may provide the threshold value used for the body motion determination with hysteresis. In particular, for example, with a first threshold value and a second threshold value larger than the first threshold value set in advance, under the condition that the subject S is determined as with no body motion arising therein, as far as the simple average $\sigma s_{AV}$ is yet smaller than the second threshold value, the subject S is not determined as with a body motion arising therein. On the other hand, under the condition that the subject S is determined as with a body motion arising therein, even if the simple average $\sigma s_{AV}$ is smaller than the second threshold value, the subject S is not determined as with no body motion arising therein, but is determined as with no body motion arising therein at the point of the simple average $\sigma s_{AV}$ becoming smaller than the first threshold value.

In the biological state monitoring system 100 of the above embodiment, the body motion determining unit 33 may determine whether or not the subject S has a body motion on the basis of a comparison between at least one of the standard deviations $\sigma_1$ to $\sigma_4$ and the threshold value, or a comparison between the total value or a simple average of at least two or more of the standard deviations $\sigma_1$ to $\sigma_4$ and the threshold value, without finding the normalized standard deviations $\sigma s_1$ to $\sigma s_4$.

In the biological state monitoring system 100 of the above embodiment, the body motion determining unit 33 can also determine whether or not the subject S has a body motion without using the standard deviations $\sigma_1$ to $\sigma_4$. In particular, for example, it determines whether or not the subject S has a body motion on the basis of a movement of the center of gravity of the subject S.

As described earlier on, the center of gravity G of the subject S oscillates in the direction of the body axis SA of the subject S according to the respirations of the subject S (FIG. 5(a)). Further, the center of gravity G of the subject S moves according to that if the subject S has a small body motion or a large body motion. Then, the moving distance of the center of gravity G over a predetermined period increases in the ascending order of the period when the subject S only respires, the period when the subject S has a small body motion, and the subject S has a large body motion.

Therefore, the body motion determining unit 33 can determine whether or not the subject S has a body motion by comparing a predetermined threshold value with the moving distance of the center of gravity G over a predetermined period. In particular, for example, it is possible to determine that the subject S has a small body motion if the moving distance D of the center of gravity G over a predetermined period is longer than a threshold value $D_{th}$.

The biological state monitoring system 100 of the above embodiment does not need to include all of the load detectors 11 to 14 but may include only any one of the four. For example, if there are three such load detectors, then it is still possible to detect the position of the center of gravity G of the subject S on the plane of the bed BD provided that the three load detectors are not arranged on a straight line. Further, the load detectors do not need to be arranged at the four corners of the bed but may be arranged in any positions as far as they can detect the load of the subject on the bed and the variation thereof. Further, the load detectors 11 to 14 are not limited to load sensors using beam-type load cells but, for example, force sensors are also usable.

Figure 9:
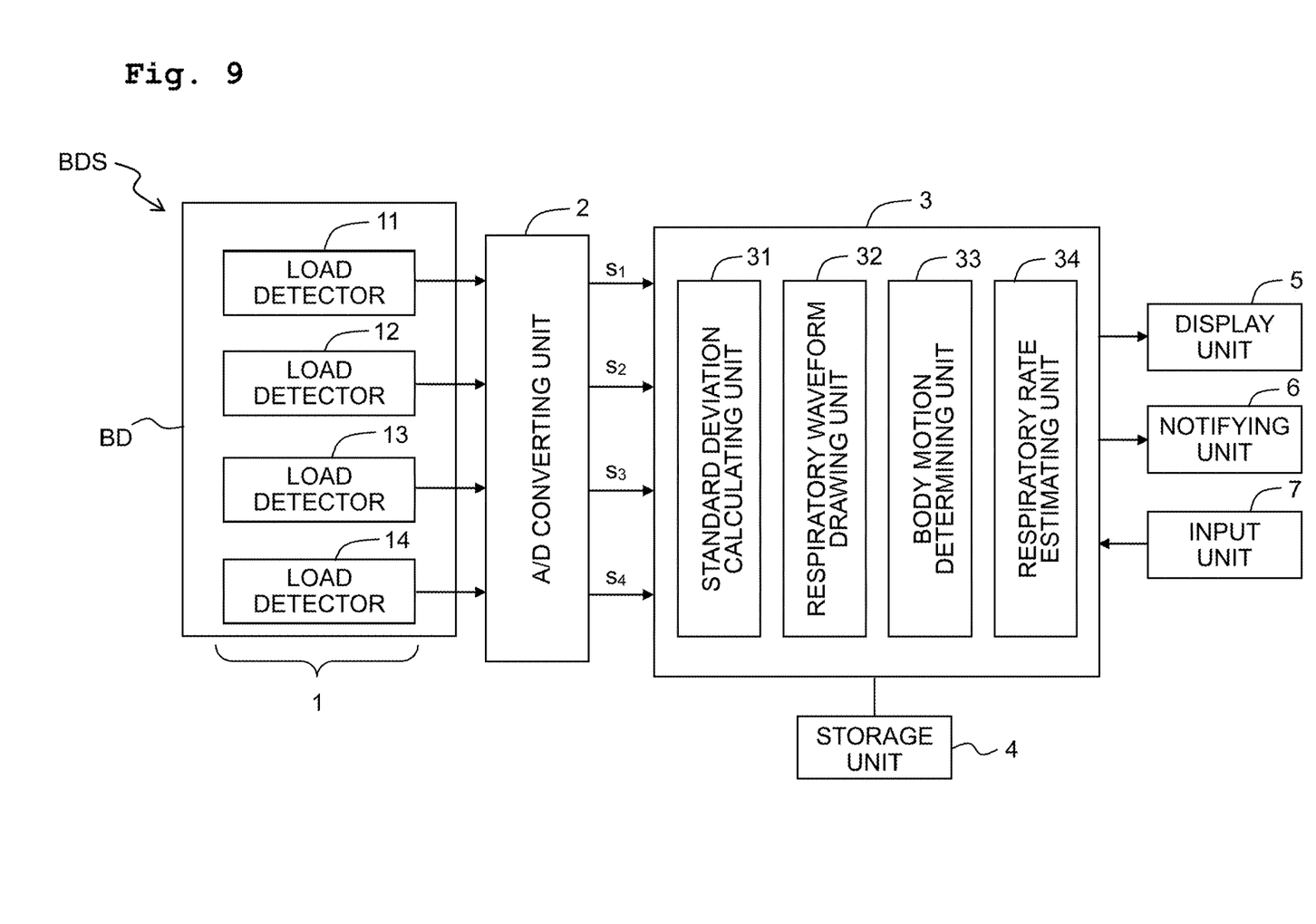
FIG. 9 is a block diagram depicting an overall configuration of a bed system according to a modified embodiment of the present invention.

In the biological state monitoring system 100 of the above embodiment, the load detectors 11 to 14 are arranged respectively on the undersides of the casters C attached to the lower ends of the legs of the bed BD. However, there is no limitation thereto. Each of the load detectors 11 to 14 may be provided respectively between one of the four legs of the bed BD and the board of the bed BD. Alternatively, if each of the four legs of the bed BD can be divided into upper and lower portions, each of the load detectors 11 to 14 may be provided between the upper leg and the lower leg. Further alternatively, the load detectors 11 to 14 may be formed integral with or removable from the bed BD to construct a bed system BDS comprising the bed BD, and the biological state monitoring system 100 of this embodiment (FIG. 9).

In the biological state monitoring system 100 of the above embodiment, between the load detecting unit 1 and the A/D converting unit 2, it is possible to provide a signal amplifying unit to amplify the load signals fed from the load detecting unit 1, and a filtering unit to eliminate the noises from the load signals.

In the biological state monitoring system 100 of the above embodiment, the display unit 5 may include a printer for printing out the information indicating the biological state (respiratory rate, presence or absence of body motion, etc.), a simplified visual display means such as lamps indicating the biological state (respiratory rate, presence or absence of body motion, etc.), and/or the like, instead of the monitor or in addition to the monitor. Further, the notifying unit 6 may include a vibration generating unit for performing the notification by way of vibration, instead of the speaker or in addition to the speaker.

The present invention is not limited to the embodiment described above provided that the feature of the present invention is maintained. Other embodiments, which are conceivable within the scope of the technical concept of the present invention, are also included in the scope of the present invention.

INDUSTRIAL APPLICABILITY

According to the biological state monitoring system of the present invention, it is possible to suppress the influence of body motion of the subject so as to estimate the respiratory rate of the subject with high precision. Therefore, by using the biological state monitoring system of the present invention, it is possible to provide high-quality medical treatments and caregiving services on the basis of the high-precision estimation of the respiratory rate.

PARTS LIST

1: load detecting unit, 11, 12, 13, 14: load detector, 2: A/D converting unit, 3: control unit, 31: standard deviation calculating unit, 32: respiratory waveform drawing unit, 33: body motion determining unit, 34: respiratory rate estimating unit, 4: storage unit, 5: display unit, 6: notifying unit, 7: input unit, 100: biological state monitoring system, BD: bed, BDS: bed system, S: subject.

The invention claimed is:

1. A biological state monitoring system for monitoring a biological state of a subject on a bed over a predetermined monitoring period, the system comprising:
- a plurality of load detectors each configured to detect a load value of the subject on the bed; and
- a controller configured to:
  - successively obtain and output estimated values of a respiratory rate of the subject, based on a temporal variation of the load value detected over time by at least one of the plurality of load detectors;
  - obtain a center of gravity position of the subject based on the load value detected by each of the plurality of load detectors;
  - obtain a respiratory waveform of the subject based on a temporal variation of the center of gravity position of the subject; and
  - determine whether or not the subject has a body motion based on a comparison between a threshold value and a standard deviation of the temporal variation of the load value of the subject detected by at least one of the plurality of load detectors,
- wherein the controller is configured to compensate the standard deviation to be used in the comparison by dividing the standard deviation by an amplitude of the respiratory waveform, and
- wherein the controller is configured to output, from a body motion occurrence time until passing of a predetermined period after a body motion ending point, a last estimated value of the respiratory rate of the subject which is the latest among the estimated values of the respiratory rate of the subject obtained prior to the body motion occurrence time, the body motion occurrence time being a time point at which the controller determines that the subject has the body motion, the body motion ending point being a time point at which the controller determines that the subject has no body motion for the first time after the body motion occurrence time.

2. The biological state monitoring system according to claim 1,
- wherein the controller is configured to obtain the estimated values of the respiratory rate of the subject based on the respiratory waveform.

3. The biological state monitoring system according to claim 2, wherein the controller is configured to:
- obtain an average of inter-peak distances of the respiratory waveform, of the subject, obtained within a predetermined sampling period, the inter-peak distance being a distance between two adjacent peaks of the respiratory waveform; and
- obtain the estimated values of the respiratory rate of the subject by using the equation of $R=60/t_{AV}$, provided that $t_{AV}$ is the average of the inter-peak distances, in seconds, and R is the estimated value of the respiratory rate in one minute of the subject.

4. The biological state monitoring system according to claim 2, wherein the controller is configured to:
- obtain, after the passing of the predetermined period after the body motion ending point an inter-peak distance between first and second peaks of the respiratory waveform of the subject, the first and second peaks being firstly and secondly exhibited peaks after the body motion ending point, respectively; and
- obtain and output the estimated value of the respiratory rate of the subject by using the equation of $R=60/t$, provided that t is the inter-peak distance, in seconds, and R is the estimated value of the respiratory rate in one minute of the subject.

5. The biological state monitoring system according to claim 3, wherein a length of the predetermined period after the body motion ending point is substantially equal to a length of the predetermined sampling period.

6. The biological state monitoring system according to claim 1, further comprising a display configured to display the estimated values of the respiratory rate of the subject, outputted by the controller.

7. A bed system comprising:
- a bed; and
- the biological state monitoring system as defined in claim 1.

8. A biological state monitoring system for monitoring a biological state of a subject on a bed over a predetermined monitoring period, the system comprising:
- a plurality of load detectors each configured to detect, over time, a load value of the subject on the bed; and
- a controller configured to:
  - obtain a center of gravity position of the subject based on the load value detected by each of the plurality of load detectors;
  - obtain a respiratory waveform of the subject based on a temporal variation of the center of gravity position of the subject;
  - successively obtain and output estimated values of a respiratory rate of the subject, based on the respiratory waveform of the subject; and
  - determine whether or not the subject has a body motion based on dividing a standard deviation of a temporal variation of the load value detected by at least one of the plurality of load detectors by an amplitude of the respiratory waveform,
- wherein the monitoring period includes a body motion period in which the subject has the body motion, and a resting period in which the subject merely performs a respiration,
- wherein, in a case that the monitoring period shifts from a first resting period to the body motion period and then from the body motion period to a second resting period, the controller is configured to output, in the body motion period and a period after shifting from the body motion period to the second resting period, a last estimated value of the respiratory rate of the subject which is the latest among the estimated values of the respiratory rate of the subject obtained successively in the first resting period, and
- wherein the controller is configured to:
  - obtain an inter-peak distance between two peaks of the respiratory waveform of the subject, the two peaks being firstly and secondly exhibited peaks of the respiratory waveform in the second resting period;

obtain the estimated value of the respiratory rate of the subject by using the equation of R=60/t, provided that t is the inter-peak distance, in seconds, and R is the estimated value of the respiratory rate in one minute of the subject; and output the obtained estimated value instead of the last estimated value which is the latest among the estimated values obtained successively in the first resting period.

9. The biological state monitoring system according to claim 8, wherein the controller is configured to:

obtain an average of inter-peak distances of the respiratory waveform, of the subject, obtained within a predetermined sampling period, the inter-peak distance being a distance between two adjacent peaks of the respiratory waveform; and obtain the estimated values of the respiratory rate of the subject by using the equation of $R=60/t_{AV}$, provided that $t_{AV}$ is the average of the inter-peak distances, in seconds, and R is the estimated value of the respiratory rate in one minute of the subject.

10. The biological state monitoring system according to claim 9, wherein the controller is configured to output, after the predetermined sampling period has been passed after the shifting to the second resting period, the estimated value of the respiratory rate of the subject obtained by the equation of $R=60/t_{AV}$.

11. The biological state monitoring system according to claim 8, further comprising a display configured to display the estimated values of the respiratory rate of the subject, outputted by the controller.

12. A bed system comprising:
a bed; and
the biological state monitoring system as defined in claim 8.

* * * * *